United States Patent [19]

Moo-Young et al.

[11] Patent Number: 5,116,747
[45] Date of Patent: May 26, 1992

[54] IMMOBILIZATION OF BIOLOGICALLY ACTIVE MATERIAL IN CAPSULES PREPARED FROM A WATER-SOLUBLE POLYMER AND CHITOSAN ACETATE

[75] Inventors: Murray Moo-Young; Niels C. Bols, both of Waterloo; Sandra E. Overgaard, Perth; Jeno M. Scharer, Waterloo, all of Canada

[73] Assignee: University of Waterloo, Waterloo, Canada

[21] Appl. No.: 392,351

[22] Filed: Aug. 11, 1989

[51] Int. Cl.⁵ .................. C12N 11/10; C12N 11/02; C12P 21/08
[52] U.S. Cl. .................. 435/178; 435/70.2; 435/70.21; 435/177; 435/182
[58] Field of Search ............ 435/177, 178, 182, 70.2, 435/70.21; 424/93

[56] References Cited

U.S. PATENT DOCUMENTS

| | | | |
|---|---|---|---|
| 4,352,883 | 10/1982 | Lim | 435/182 X |
| 4,749,620 | 6/1988 | Rha et al. | 424/93 X |
| 4,803,168 | 2/1989 | Jarvis, Jr. | 435/178 |
| 4,808,707 | 2/1989 | Daly et al. | 435/178 X |
| 4,921,796 | 5/1990 | Rozzell | 435/97 |

*Primary Examiner*—David M. Naff
*Attorney, Agent, or Firm*—Sim & McBurney

[57] ABSTRACT

Biologically-active material, particularly hybridoma cells, is immobilized for mass culture in bioreactors to produce biological products, particularly monoclonal antibodies, by ionically-interacting polycationic groups on chitosan with polyanionic groups on a polyanionic water-soluble polymer. Preferably, the chitosan is chitosan acetate and the polyanionic polymer is sodium alginate. In one embodiment, droplets of a suspension of the biologically-active material and water-soluble polymer are gelled by forming a calcium salt of the water-soluble polymer to form temporary capsules, and a sequestering agent for the calcium ions is added to effect ionotropic gelation of the water-soluble polymer and chitosan to form a semi-permeable membrane around each temporary capsule. In another embodiment, porous beads are formed by exposing droplets of a suspension of the biologically active material and water-soluble polymer to an aqueous solution of chitosan and multiple cations. In a further embodiment, chitosan is added to a suspension of the biologically active material and water-soluble polymer and the resulting suspension is extruded into a solution of multi-valent anions to form a fibrous mass.

23 Claims, No Drawings

IMMOBILIZATION OF BIOLOGICALLY ACTIVE MATERIAL IN CAPSULES PREPARED FROM A WATER-SOLUBLE POLYMER AND CHITOSAN ACETATE

FIELD OF INVENTION

The present invention is concerned with the immobilization of biologically-active materials including biological cells, particularly hybridomacells, for use in bioreactors for the production of biological products.

BACKGROUND TO THE INVENTION

Various attempts have been made to encapsulate and otherwise immobilize biological cells so that they remain viable and in a protected state within a semipermeable membrane which permits the passage into the capsule of nutrients, oxygen and other species required for sustaining cell viability and metabolic functions and which also permits cell metabolites to pass out of the capsules.

In one prior art process, described in U.S. Pat. No. 4,251,387, capsules are manufactured by interfacial polymerization effected by reacting cationic monomers containing multifunctional amine groups with complementary anionic species. Polyelectric complex formation is accomplished by the formation of salt-bridges between anionic and cationic species.

Prior art immobilization procedures generally have suffered from one or more of the drawbacks of high material costs, high potential for contamination during the immobilization process, oxygen and nutrient limitations in the immobilized cell matrices, mechanical and/or chemical instability of the immobilized cell matrices, a narrow range of biocompatibility of matrix materials with cells and the use of expensive weighting materials.

SUMMARY OF INVENTION

In accordance with the present invention, there is provided a novel procedure for immobilizing biological cells and other biologically-active materials to enable them to be used in bioreactors for the production of a wide variety of biological products, including monoclonal antibodies, vaccines and pharmaceuticals.

By immobilizing the cells using the present invention, the cells are able to proliferate in concentrations significantly higher than for non-immobilized conditions and to remain viable within the immobilization matrices. The immobilized cells are particularly applicable to large-scale operations as required for industrial manufacturing. The immobilization procedures promote the essential mass transfer of nutrients, including oxygen, to the cells and the desirable passage of waste metabolites from the immobilized cells.

In the present invention, the process of immobilization is effected using chitosan as the key immobilizing agent. A solid immobilizing medium is formed for the biologically-active materials and cells by ionic interaction of polycationic groups on the chitosan with polyanionic groups on a polyanionic polymer. The procedure of immobilization may be effected in any convenient manner, including encapsulation, entrapment and occlusion.

GENERAL DESCRIPTION OF INVENTION

In the present invention, the immobilization may be effected using one of three different, but related, procedures, namely encapsulation, entrapment and occlusion. Essential to the present invention is the use of chitosan, a partially deacetylated chitin. Chitosan is a polycationic polymeric material having free amino acid groups, which are protonated for use in the present invention. The molecular weight of the chitosan may be varied to vary the properties of the immobilized product. Generally, the chitosan has an average molecular weight of about $5 \times 10^5$ to about $20 \times 10^5$, preferably about $5 \times 10^5$ to about $15 \times 10^5$. Chitosan is biocompatible, mechanically-stable, inexpensive and provides good mechanical protection to the cells. The chitosan may be employed in a variety of mild polymerization processes involving ionic interactions between polycationic and polyanionic polymers to immobilize the cells.

(a) Encapsulation Method

In this embodiment of the invention, the cells are encapsulated within an outer semi-permeable membrane which is an ionically-interacted combination of chitosan and alginate or other polyanionic polymer. The semipermeable membrane is permeable to nutrients, ions and other low molecular weight materials required for sustaining cell viability and metabolic functions. Depending on permeability, the membrane may or may not be permeable to the product secreted from the cells.

Once encapsulated, the immobilized cells in the microcapsules then are cultivated in aqueous culture medium.

The cells are suspended in an aqueous solution of a polyanionic polymer, such as a polysaccharide gum, which can be reversibly gelled, generally an alkali metal alginate, preferably sodium alginate. The suspension then is formed into droplets by passing the suspension through any convenient droplet-forming apparatus and the droplets are gelled in an aqueous solution of calcium chloride to form temporary capsules. The droplet-forming apparatus generally is capable of forming droplets of such a size that the final microcapsules have a diameter from about 500 to about 3000 microns, preferably about 500 to about 1000 microns. The temporary capsules then are contacted with an aqueous solution of chitosan, which usually is in the form of a quaternary salt, such as the acetate. The aqueous solution of chitosan generally has a concentration of about 0.15 to about 3 wt.%, preferably about 1 to about 2 wt.%. The whole procedure is effected at a pH of about 5.6 to 6.0 to ensure that the free amino groups on the chitosan are protonated.

A sequestering agent for calcium, preferably sodium phosphate, then is slowly added to the mixture to cause precipitation of calcium phosphate. Ionotropic gelation then takes place between the protonated amino groups on the chitosan and the freed carboxylic groups on the alginate, to form a coating on the surface of each of the beads, so as to encapsulate the cells.

The coating or semipermeable membrane, which is formed in a period generally of about 1 to about 20 minutes, preferably about 4 to about 6 minutes, generally has a thickness of about 2 to about 10 microns, preferably about 5 to about 10 microns.

The majority of the calcium alginate remains in that form during the encapsulation step. The calcium alginate may be reliquified by sequestering the calcium ions, such as by exposure to sodium citrate solution.

The permeability and structural integrity of the chitosan-alginate microcapsules may be altered during membrane formation by varying the concentration and molecular weight of the polycationic polymer (i.e., the chitosan) within the ranges noted above, as well as the duration of the ionotropic gelation.

(b) Entrapment Method

In this embodiment of the invention, the cells are impregnated within the pores of chitosan-stabilized calcium alginate beads. The metabolic product of the cells is excreted into the growth medium from the pores, permitting batch or continuous operation of a bioreactor vessel in which the beads are retained and may be reused.

The cells are suspended in an aqueous solution of a polyanionic polymer which can be gelled, such as a polysaccharide gum, generally an alkali metal alginate, preferably sodium alginate. The suspension then is formed into droplets by passing the suspension through any convenient droplet-forming apparatus. The droplet-forming apparatus generally is capable of forming droplets of such a size that the final beads have a diameter from about 500 to about 3000 microns, preferably about 500 to about 1000 microns.

The droplets then are passed into an aqueous solution containing the chitosan, which usually is in the form of a quaternary salt, such as the acetate. The aqueous solution of chitosan generally has a concentration of about 0.1 to about 1 wt.%, preferably about 0.5 to about 1 wt.%. The procedure is effected at a pH of 5.6 to 6.0 to ensure that the free amino groups on the polycationic chitosan are protonated. The solution into which the droplets are extruded also contains additional counterions, usually calcium, present as calcium chloride. Competition between the calcium and the cationic moieties on the chitosan results in the formation of highly cross-linked and hardened porous beads. The gelation proceeds for about 5 to about 30 minutes, preferably about 10 to about 20 minutes.

(c) Occlusion Method

In this embodiment of the invention, the cells are immobilized within the pores of a fibrous chitosan-alginate matrix. The metabolic product of the cells is excreted into the growth medium from the pores in the fibrous matrix, permitting continuous operation of a bioreactor vessel in which the fibrous matrix is used.

The cells are suspended in an aqueous solution of a polyanionic polymer, generally an alkali metal alginate, preferably sodium alginate. The chitosan, which usually is in the form of a quaternary ammonium salt, such as the acetate, then is added to the suspension, resulting in the formation of a soluble polyelectric complex with the polyanionic polymer. The chitosan solution generally has a concentration of about 0.1 to about 2 wt.%, preferably about 0.5 to about 1 wt.%. The suspension is maintained at a pH of about 5.6 to 6.0 to ensure that the free amino groups on the chitosan are protonated.

The suspension then is extruded into an aqueous cross-linking and hardening solution containing multivalent anions, such as a pyrophosphate, preferably sodium pyrophosphate, and having a mildly alkaline pH, preferably about 7.3 to 7.5, resulting in fibre formation in which the cells are occluded within pores. The cross-linking proceeds for about 1 to about 10 minutes, preferably about 4 to about 6 minutes. Control of fiber porosity is accomplished by altering the duration of the cross-linking of the polyelectrolytes.

EXAMPLES

Example I

This Example illustrates the immobilization of hybridoma cells by encapsulation and growth of the immobilized cells in culture.

HP-6 murine hybridoma cells which produce monoclonal antibodies (MAb) directed against horse radish peroxidase were cultivated to a density of approximately $10^6$ cells/mL in Dulbecco's Modified Eagle's Medium (DMEM) supplemented with 10% fetal calf serum at 37° C. in a 5% $CO_2$ air-based environment.

M4-1 murine hybridoma cells producing MAbs against bovine light chain $IgG_1$ also were grown under the same environmental conditions to a density of about $10^6$ cells/mL in Modified Eagle's Medium (MEM) supplemented with 10% horse serum.

5 mL of each hybridoma cell suspension was mixed with 5 mL of a 3% (w/v) sodium alginate solution (pH=5.6 to 6). The cell-alginate solution then was formed into droplets by passing the suspension through a droplet forming apparatus.

The droplet-forming apparatus consisted of a 20 cc syringe equipped with a 0.01 inch I.D. Teflon (trademark for polytetrafluoroethylene) coated needle. The syringe and needle assembly were positioned within a plexiglass housing such that the tip of the needle was subjected to a constant laminar air flow which acted as an air knife. A constant force applied to the top of the housing forced droplets of the cell-alginate suspension contained within the syringe from the tip of the needle. Each drop was disengaged from the needle tip by the laminar air stream and allowed to fall approximately 5 cm into a 50 mM $CaCl_2$ solution (pH 5.6 to 6) wherein it was cross-linked to form a shape-retaining protective temporary bead. The bead size was controlled to be within the range of 900 to 1200 microns by adjusting the flow rate of the air stream.

After bead hardening for 5 to 20 minutes in the calcium chloride solution and washing with 125 mM NaCl (pH 5.6 to 6), a semi-permeable capsule membrane was formed by thoroughly coating the gelled beads with an aqueous 2% (w/v) chitosan-acetate solution (pH 5.6 to 6), followed by the slow addition of enough sodium phosphate (24.2 g/L monobasic and 3.5 g/L dibasic, pH 5.6 to 6), to cause the precipitation of calcium phosphate. Ionotropic gelation between the protonated amino groups on the chitosan and the carboxylic groups on the alginate proceeded for 5 minutes.

The calcium alginate within the resulting microcapsules was reliquified by exposing the capsules to 110 mM sodium citrate (pH 7) for 2 to 4 minutes. After a thorough washing in 125 mM NaCl, the resultant microcapsules (approximately 1,100 microns in diameter) were resuspended in tissue culture medium and were transferred to 75 $cm^3$ culture flasks for incubation at 37° C. and 5% $CO_2$.

For comparative purposes, HP-6 hybridoma cells from the same stock culture also were grown in conventional tissue culture flasks according to two known methods, namely (1) conventional batch suspension and (2) immobilized in polylysine microcapsules of the same size prepared according to the procedure described in U.S. Pat. No. 4,251,387 referred to above. The maximum viable cell densities for the three HP-6 hybridoma cell cultures were determined at a suitable period, usually 5 to 20 days of culture, and the results obtained are tabulated in the following Table I:

TABLE I

|  | Chitosan-alginate | Polylysine | Suspension |
|---|---|---|---|
| Max. Viable Conc. in Capsules (cells/mL) | $4.5 \times 10^7$ | $5.9 \times 10^6$ | — |
| Max. Effective Viable Conc.* (cells/mL culture) | $1.1 \times 10^7$ | $1.7 \times 10^6$ | $8.0 \times 10^5$ |

*Microcapsules occupied 25% of total culture volume.

As may be seen from the results set forth in Table I, the microcapsules prepared according to the present invention produce significantly higher viable cell densities than simple suspension culturing and microencapsulation by prior art procedures.

Example 2

This Example illustrates the immobilization of hybridoma cells by entrapment in beads and growth of the immobilized cells in culture.

A 5 mL suspension of hybridoma cells ($10^6$ cells/mL) was mixed with 5 mL of a 3% (w/v) sodium alginate solution (pH 5.6 to 6). The cell-alginate suspension then was passed through the droplet forming apparatus as described in Example 1 above, into a gently stirred solution containing one part 2% (w/v) chitosan-acetate solution (pH 5.6 to 6) and two parts 50 mM $CaCl_2$ (pH 5.6 to 6). The ionotropic gelation of chitosan and calcium with alginate proceeded for a maximum of 20 minutes. The hardened beads were washed twice with 125 mM NaCl followed by one wash with DMEM or MEM. The procedure was effected for both the HP-6 and M4-1 hybridoma cells described in Example 1.

The resultant chitosan-alginate beads, (approximately 1,000 microns in diameter), then were transferred to conventional tissue culture flasks and were cultivated at 37° C. and 5% $CO_2$. The immobilized cells were cultivated in a batch-mode for the first 5 days of the culture period. After this initial time, the cell culture was operated semi-continuously by exchanging approximately 70% of the medium daily for the duration of the culture.

For comparative purposes, HP-6 hybridoma cells from the same stock culture also were grown in tissue culture flasks by conventional batch suspension. The maximum viable cell densities and monoclonal antibody production for the two HP-6 hybridoma cell cultures were determined at a suitable material, usually from 5 to 20 days of culture, and the results are tabulated in the following Table II:

TABLE II

|  | Chitosan Beads | Suspension |
|---|---|---|
| Effective Viable Cell Density at Harvest (cells/tot. vol.) | $1.7 \times 10^6$ | $4.8 \times 10^5$ |
| Vol. Productivity (ug/mL medium-hr) | 0.38 | 0.19 |

As may be seen from the results set forth in Table II, the cells immobilized according to the invention produced a higher cell growth and MAb production than conventional batch suspension cultures.

HP-6 cells also were immobilized in agarose beads of diameter 1000 microns following the procedure of Nilsson et al referred to above and the cell growth in culture compared with the HP-6 hybridoma cells immobilized as described above. The results are set forth in the following Table III:

TABLE III

|  | Chitosan-alginate | Agarose |
|---|---|---|
| Max. Viable Cell Conc. in beads (cells/mL) | $1.3 \times 10^7$ | $5.2 \times 10^6$ |
| Effective Viable Cells Conc. (cell/mL tot. vol.) | $1.7 \times 10^6$ | $7.1 \times 10^5$ |
| Maximum Specific Growth Rate ($hr^{-1}$) | .03 | .03 |

As may be seen from these results, a higher overall cell growth was experienced for the cells immobilized according to the present invention.

Example 3

This Example illustrates the immobilization of hybridoma cells by occlusion in fibers and growth of the immobilized cells in culture.

A 5 mL cell culture suspension containing approximately $10^6$ cells/mL was centrifuged at 2000 RPM for 5 minutes. The resultant cell pellet was resuspended in 10 mL of a 1.5% (w/v) sodium alginate solution (pH 5.6 to 6). Ten mL of a 0.5% (w/v) chitosan-acetate solution (pH 5.6 to 6) was then added to the cell-alginate suspension and mixed well. The cell-alginate-chitosan suspension was immediately extruded into a gently stirred 1.5% (w/v) sodium pyrophosphate solution (pH 7.3 to 7.5) using the needle and syringe assembly described above in Example 1 (but omitting the air knife). After crosslinking for 4 minutes, the fibers were washed extensively with 125 mM NaCl and then once with tissue culture medium. The procedure was effected for both HP-6 and M4-1 hybridoma cells described in Example 1.

Cells occluded within the pores (40 to 60 microns in diameter) of the fibrous chitosan-alginate matrix were cultivated in stationary flasks and in 1 L airlift (internal-loop) and 0.5 L bubble columns. After 5 days of batch culture, between 75 to 80% of the medium was exchanged daily for the duration of the culture period. Immobilized cultures were operated semi-continuously for over 1 month.

The viable cell densities and monoclonal antibody production for the HP-6 hybridoma cells immobilized by the occlusion procedure described above were compared with those produced by the same cells grown in conventional batch suspension. The results obtained are set forth in the following Table IV:

TABLE IV

|  | Chitosan Fibers[1] | Suspension |
|---|---|---|
| Approx. Viable Cell Conc. at Harvest (cells/mL fiber) | $1.6 \times 10^7$ | — |
| Effective Viable Cell Conc. at Harvest (cells/mL tot. vol.) | $2.8 \times 10^6$ | $4.8 \times 10^5$ |
| MAb Titre of harvest liquor[2] (ug/mL) | 20 | 30 |
| Vol. Productivity[3] (ug/mL medium-hr) | 0.71 | 0.19 |

[1] 100 mL total volume and 16 mL fiber volume.
[2] MAb was harvested daily in the immobilized system after day 6.
[3] A turn around time of 12 hours for the batch reactor has been assumed.

As may be seen from these results, a significantly higher cell density and MAb productivity was obtained by occlusion of the fibers, according to the invention.

What we claim is:

1. A process for immobilizing, in the form of capsules, biologically-active material, with retained viability, which comprises:

suspending said biologically-active materials in aqueous culture medium containing a water-soluble polymer having multiple anionic reactive groups that are readily ionized, forming the resulting suspension into droplets, gelling the droplets to form water-insoluble temporary capsules by forming the calcium salt of said water-soluble polymer, coating the surface of the temporary capsules with chitosan acetate, and adding a sequestering agent for the calcium ions to effect ionotropic gelation of the water-soluble polymer and chitosan acetate to form a semi-permeable membrane around each capsule.

2. The process of claim 1 wherein said water-soluble polymer is a polysaccharide gum.

3. The process of claim 2 wherein said polysaccharide gum is sodium alginate.

4. The process of claim 1 wherein said sequestering agent is sodium phosphate.

5. The process of claim 1 wherein said ionotropic gelation is effected at a pH of about 5.6 to 6.0.

6. The process of claim 1 wherein said biological-active material produces biological substances and said semi-permeable membrane has a permeability to permit nutrients and oxygen to flow from a bulk active medium to the biological material and such biological substances to flow into the bulk active medium.

7. The process of claim 1 wherein said biologically-active material produces biological substances and said semipermeable membrane has a permeability to permit nutrients and oxygen to flow from a bulk active medium to the biological material and to retain the biological material within the microcapsule.

8. The process of claim 1 wherein said biological material is hybridoma cells.

9. The process of claim 1 wherein said biologically-active material is cells.

10. A process for immobilizing biologically-active material in the form of porous beads, with retained viability, which comprises:

suspending the biologically-active material in an aqueous culture medium containing a water-soluble polymer having multiple ionic reactive groups, forming the resulting suspension into droplets, and exposing said droplets to an aqueous solution containing (i) chitosan acetate and (ii) multiple counter-ions at a pH of about 5.6 to 6.0, whereby said chitosan acetate and said multiple counter-ions compete for ionic sites on the water-soluble polymer to form porous beads in which the biological material is impregnated within the pores.

11. The process of claim 1 wherein said water-soluble polymer is a polysaccharide.

12. The process of claim 11 wherein said polysaccharide is sodium alginate.

13. The process of claim 11 wherein said source of multiple counter-ions in said aqueous solution is calcium chloride.

14. The process of claim 11 wherein said biologically-active material is hybridoma cells.

15. The process of claim 10 wherein said biologically-active material is cells.

16. A process for immobilizing, in the form of porous fibers, biologically-active material with retained viability, which comprises:

suspending the biologically-active material in a physiologically-compatible medium containing a water-soluble polymer with multiple anionic moieties, adding chitosan acetate to the resulting suspension to form a polyelectric complex with the water-soluble polymer, and extruding the resulting suspension into an aqueous cross-linking solution containing multi-valent anions to form a fibrous mass.

17. The process of claim 16 wherein said water-soluble polymer is a polysaccharide gum.

18. The process of claim 17 wherein said polysaccharide gum is sodium alginate.

19. The process of claim 16 wherein said multivalent anions in said cross-linking solution are provided by sodium pyrophosphate.

20. The process of claim 16 wherein said polyelectric complex is formed at a pH of about 5.6 to 6.0.

21. The process of claim 20 wherein said aqueous cross-linking solution has a pH of about 7.2 to 7.4.

22. The process of claim 16 wherein said biological material is hybridoma cells.

23. The process of claim 16 wherein said biologically active material is cells.

* * * * *